United States Patent
Abraham et al.

(10) Patent No.: US 9,588,239 B2
(45) Date of Patent: Mar. 7, 2017

(54) DATA ACQUISITION SYSTEM OF PHOTON COUNTING DETECTOR ARRAY

(71) Applicant: Analogic Corporation, Peabody, MA (US)

(72) Inventors: Douglas Abraham, Topsfield, MA (US); David Rozas, Brighton, MA (US); Anton Deykoon, Arlington, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 9 days.

(21) Appl. No.: 14/693,370

(22) Filed: Apr. 22, 2015

(65) Prior Publication Data
US 2016/0313457 A1    Oct. 27, 2016

(51) Int. Cl.
  *G01T 1/24*    (2006.01)
  *G01T 1/164*   (2006.01)
  *A61B 6/00*    (2006.01)

(52) U.S. Cl.
  CPC ........... *G01T 1/247* (2013.01); *A61B 6/4241* (2013.01); *G01T 1/1642* (2013.01)

(58) Field of Classification Search
  USPC ............... 378/98.8, 91; 250/370.09, 370.08
  See application file for complete search history.

(56) References Cited

U.S. PATENT DOCUMENTS

| 2008/0099689 A1* | 5/2008 | Nygard | G01T 1/2018 |
| | | | 250/370.09 |
| 2015/0069255 A1* | 3/2015 | Abraham | G01T 1/17 |
| | | | 250/393 |

* cited by examiner

*Primary Examiner* — Kiet T Nguyen
(74) *Attorney, Agent, or Firm* — Cooper Legal Group, LLC

(57) ABSTRACT

Among other things, one or more techniques and/or systems are described for generating an output of a detector cell of a photon counting detector array. A counter block generates integration data and photon counting data associated with the photon counting detector array. Responsive to a number of detection events counted during a measurement interval (e.g., a view) not exceeding a first detection event count threshold, a first output may be generated based upon the photon counting data. Responsive to the number of detection events exceeding a second detection event count threshold, a second output may be generated based upon the integration data. Responsive to the number of detection events being between the first detection event count threshold and the second detection event count threshold, a blended output may be generated based upon the photon counting data and the integration data.

20 Claims, 9 Drawing Sheets

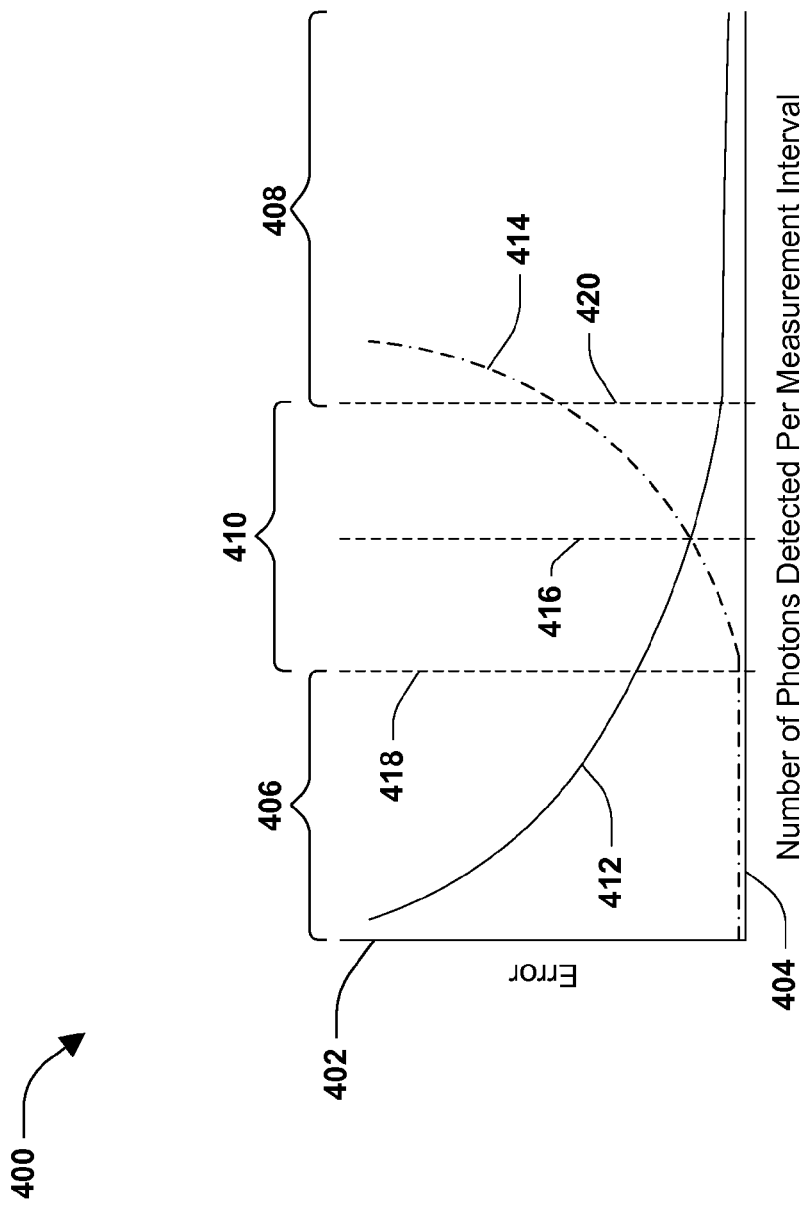

DATA ACQUISITION SYSTEM OF PHOTON COUNTING DETECTOR ARRAY

BACKGROUND

The present application relates to the field of radiation imaging systems. It finds particular application to data acquisition systems of radiation imaging systems that use photon counting detector arrays to measure a number and/or energy of radiation photons impinging thereon.

Today, radiation imaging systems such as computed tomography (CT) systems, single-photon emission computed tomography (SPECT) systems, projection systems, and/or line-scan systems, for example, are useful to provide information, or images, of interior aspects of an object under examination. Generally, the object is exposed to radiation comprising photons (e.g., x-rays, gamma rays, etc.), and an image(s) is formed based upon the radiation absorbed and/or attenuated by interior aspects of the object, or rather an amount of radiation photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

Radiation imaging systems typically comprise a detector array having one or more detector cells. Respective detector cells are configured to indirectly or directly convert radiation photons impingent thereon into electrical charge which is used to generate an electrical signal. The detector cells are typically "energy integrating" or "photon counting" type detector cells (e.g., the imaging system operates in energy integrating mode or photon counting mode).

Energy integrating detector cells are configured to convert radiation energy into electrical charge. The charge generated over a period of time (e.g., at times referred to as a measurement interval) is integrated to generate a signal that is proportional to an incoming radiation photon flux rate at a detector cell. While energy integrating detector cells are widely used, there are several drawbacks to this type of cell. For example, energy integrating detectors cells are generally not able to provide feedback as to the number and/or energy of radiation photons detected. As another drawback, there is a lower limit of detection defined by noise such that a detector cell with little to no incident radiation may produce some signal due to thermal and/or analog read noise (e.g., produced by a radiation conversion element and/or electronics arrangement of the detector cell). It may be appreciated that as a result of this lower limit, the dose of radiation that is applied to an object under examination is generally greater than the dose of radiation that may be applied to the object if the detector cells are of a photon counting type.

Photon counting type detector cells are configured to output a signal (e.g., a pulse) for respective detected radiation photons (e.g., where the detection of a radiation photon may be referred to as a detection event). In some embodiments, the signal (e.g., amplitude of the pulse) is indicative of a radiation energy of the detected radiation photon. A controller is configured to determine the location and energy of respective detected radiation photons based upon the pulse, accumulate the detection events occurring during a measurement interval, digitize the information, and/or process the digital information to form an image, for example. It may be appreciated that there are numerous advantages to photon counting type detector cells over energy integrating detector cells. For example, the counting of radiation photons is essentially noise free (apart from inherent photon shot noise). Therefore, a lower dose of radiation may be applied to the object under examination. Moreover, photon counting cells generally allow for energy or wavelength discrimination.

While photon counting type detector cells have numerous advantages over energy integrating detector cells, photon counting type detector cells have not been widely applied in some imaging modalities due to, among other things, saturation issues (e.g., pulse pile-up) at high radiation flux rates. For example, CT systems generally detect as many as $10^9$ radiation photons per millimeter squared of a detector per second and can detect radiation photons at even higher flux rates. At such high flux rates, the photon counting type detector cells may be unable to return to a normal state between the detection of a first radiation photon and a second radiation photon, which may cause two detection events to be counted as a single, higher energy event.

SUMMARY

Aspects of the present application address the above matters, and others. According to one aspect, an electronics arrangement of a photon counting detector array is provided. The electronics arrangement comprises an integration circuit configured to integrate charge generated by a detector cell of the photon counting detector array to generate a voltage signal. The electronics arrangement also comprises a charge injection circuit configured to inject a charge into the integration circuit in response to the voltage signal exceeding a specified threshold to reset the integration circuit. At times, the charge injected into the integration circuit in response to the voltage signal exceeding the specified threshold is referred to as an injected charge. The electronics arrangement also comprises a photon counting circuit configured to identify detection events based upon the voltage signal. The electronics arrangement further comprises a counter block. The counter block is configured to generate integration data indicative of an amount of charge integrated by the integration circuit during a measurement interval based upon a number of resets to the integration circuit during the measurement interval. The counter block is also configured to generate photon counting data indicative of a number of detection events identified by the photon counting circuit during the measurement interval. Responsive to a number of detection events during the measurement interval being between a first detection event count threshold and a second detection event count threshold, the counter block is further configured to: 1) apply a first blending weight to the integration data to create weighted integration data; 2) apply a second blending weight to the photon counting data to create weighted photon counting data; and 3) generate a blended output based upon the weighted integration data and the weighted photon counting data.

According to another aspect, a method for determining an output for a detector cell of a photon counting detector array is provided. The method comprises generating integration data indicative of an amount of charge integrated by an integration circuit during a measurement interval based upon a number of resets to the integration circuit during the measurement interval. The method also comprises generating photon counting data indicative of a number of detection events identified by a photon counting circuit during the measurement interval. The method also comprises generating a first output based upon the photon counting data responsive to the number of detection events not exceeding a first detection event count threshold for the measurement interval. The method also comprises generating a second output based upon the integration data responsive to the number of detection events exceeding a second detection event count threshold for the measurement interval. The method also comprises generating a blended output based upon the photon counting data and the integration data responsive to the number of detection events being between the first detection event count threshold and the second detection event count threshold for the measurement interval.

According to yet another aspect, a radiation imaging system is provided. The radiation imaging system comprises an ionizing radiation source and a photon counting detector array. The photon counting detector array comprises one or more detector cells configured to detect radiation from the ionizing radiation source. A first detector cell of the photon counting detector array comprises a radiation conversion element configured to convert radiation detected by the first detector cell into charge. The first detector cell also comprises an electronics arrangement. The electronics arrangement comprises an integration circuit configured to integrate the charge to generate a voltage signal and a photon counting circuit configured to identify detection events based upon the voltage signal. The electronics arrangement also comprises a counter block configured to generate integration data indicative of an amount of the charge that is integrated by the integration circuit during a measurement interval based upon a number of resets to the integration circuit during the measurement interval. The counter block is also configured to generate photon counting data indicative of a number of detection events identified by the photon counting circuit during the measurement interval. Responsive to the number of detection events being between a first detection event count threshold and a second detection event count threshold for the measurement interval, the counter block is configured to generate a blended output based upon the photon counting data and the integration data.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which:

FIG. 4 illustrates an example graph depicting the error associated with photon counting and energy integration as a function of a number of photons detected by a detector cell of a photon counting detector array.

DESCRIPTION

Figure 1:
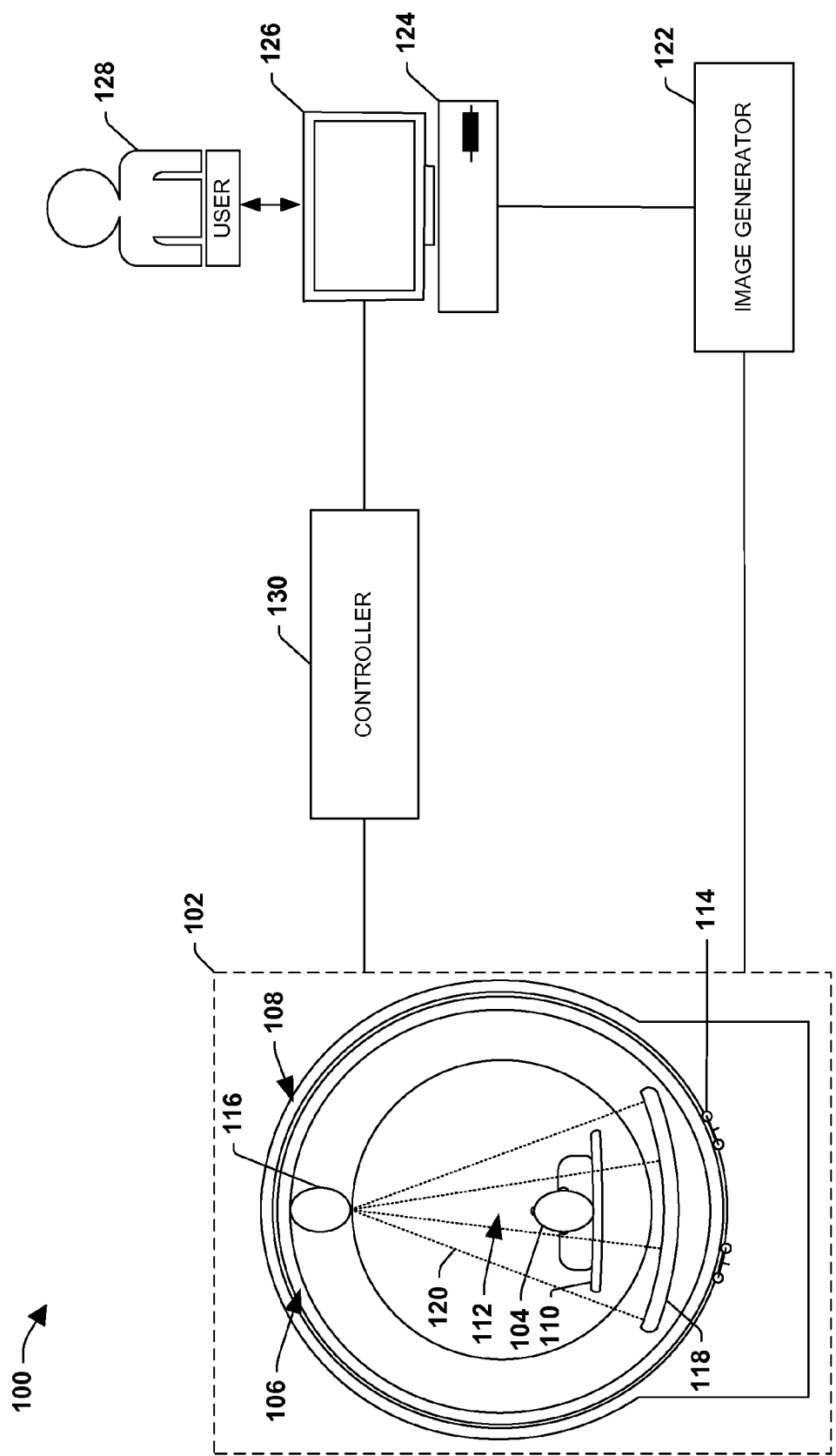
FIG. 1 illustrates an example environment of a radiation imaging system.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

A detector cell of a photon counting detector array generally comprises a radiation conversion element and an electronics arrangement (e.g., also referred to as a data acquisition system (DAS)). The radiation conversion element is configured to detect radiation photons and to convert radiation energy of the radiation photon into electrical charge (e.g., at times referred to merely as charge). The electronics arrangement is configured to use the charge to generate a voltage signal indicative of a radiation photon (e.g., indicative of the energy of the radiation photon) and to tabulate a number and/or energy of radiation photons detected by the detector cell during respective measurement intervals (e.g., where a measurement interval may correspond to a view). It may be appreciated that while the instant application describes the electronic arrangement as being part of a detector cell, the electronics arrangement may be a physically separate component which is coupled to the radiation conversion element via a communication medium (e.g., a wire, metal trace, etc.).

The electronics arrangement is configured to generate integration data indicative of electrical charge that has accumulated at the detector cell during a measurement interval and photon counting data indicative of a number of photons impingent upon the detector cell during the measurement interval. In some embodiments, the photon counting data is further indicative of energy of photons detected during detection events.

To generate the integration data, the electronics arrangement comprises an integration circuit (e.g., also referred to as a charge amplifier or a charge-to-voltage converter) and a charge injection circuit. The integration circuit is configured to convert charge, generated by the detector cell in response to a detection event, into a voltage signal by applying the charge to a capacitor of the integration circuit. The charge creates a voltage potential across the capacitor, causing a voltage signal to be generated by the integration circuit that is substantially proportional to the voltage potential across the capacitor (and in turn substantially proportional to the charge generated in response to the detection event). When the voltage potential across the capacitor exceeds a desired threshold due to the accumulation of charge at the capacitor (causing an inaccurate voltage signal to be output from the integration circuit), the charge injection circuit injects charge (at times referred to as an injected charge) into the integration circuit. The injected charge is typically opposite in polarity to the charge stored by the capacitor (referred to, at times, as stored charge) to counteract the stored charge and reset the capacitor. The integration data is indicative of the number of resets occurring within a measurement interval.

To generate the photon counting data, the electronics arrangement comprises a photon counting circuit. The photon counting circuit is configured to identify pulses in the voltage signal output by the integration circuit to identify detection events and to count those detection events. In some embodiments, the photon counting circuit also determines an energy of respective detection events based upon the identified pulses. The photon counting data is indicative of the number of detection events occurring within a measurement interval and/or the energy of respective detection events.

A counter block is configured to generate an output (data) describing measurements for the measurement interval based upon the photon counting data and/or the integration data. In some embodiments, when the number of detection events does not exceed a first detection event count threshold, the output is indicative of the photon counting data and the integration data is disregarded/ignored. When the number of detection events is above a second detection event count threshold, the output may be indicative of integration data and the photon counting data is disregarded/ignored. When the number of detection events is between the first detection event count threshold and the second detection event count threshold, the output may be indicative of the integration data and the photon counting data, i.e., the integration data may be blended with the photon counting data to generate the output.

FIG. 1 illustrates a radiation imaging system 100 comprising one or more electronics arrangements (e.g., DASs) as provided for herein. In the illustrated embodiment, the radiation imaging system 100 is a computed tomography (CT) system, although the systems and/or techniques described herein may find applicability to other radiation imaging systems such as line-scan systems, mammography systems, and/or diffraction systems, for example. Moreover, it may be appreciated that the arrangement of features, inclusion of features and/or exclusion of other features from the example radiation imaging system 100 is not intended to be interpreted in a limiting manner, such as necessarily specifying the location, inclusion, and/or relative position of the features.

The example CT system comprises an examination unit 102 configured to an examine objects 104. The examination unit 102 comprises a rotating gantry 106 and a stationary support structure 108 (e.g., which may encase and/or surround at least a portion of the rotating gantry 106 (e.g., as illustrated with an outer, stationary ring, surrounding an outside edge of an inner, rotating ring)). The examination unit 102 also comprises a support article 110, such as a bed or conveyor belt, configured to support the object 104 during an examination. In some embodiments, the support article 110 may be configured to translate the object into and/or through an examination region 112 (e.g., a hollow bore in the rotating gantry 106), where the object 104 is exposed to radiation 120, during the examination.

The rotating gantry 106 may surround a portion of the examination region 112 and may comprise a radiation source 116 (e.g., an ionizing radiation source such as an x-ray source or gamma-ray source) and a detector array 118. The detector array 118 is typically mounted on a substantially diametrically opposite side of the rotating gantry 106 relative to the radiation source 116, and during an examination of the object 104, the rotating gantry 106 (e.g., including the radiation source 116 and detector array 118) is rotated about the object 104 by a rotator 114 (e.g., belt, drive shaft, chain, roller truck, etc.). Because the radiation source 116 and the detector array 118 are mounted to the rotating gantry 106, a relative position between the detector array 118 and the radiation source 116 is substantially maintained during the rotation of the rotating gantry 106.

During the examination of the object 104, the radiation source 116 emits cone-beam, fan-beam, and/or other shaped radiation configurations from a focal spot of the radiation source 116 (i.e., a region within the radiation source 116 from which radiation 120 emanates) into the examination region 112. Such radiation 120 may be emitted substantially continuously and/or may be emitted intermittently (e.g., a brief pulse of radiation 120 is emitted followed by a resting period during which the radiation source 116 is not activated). Further, the radiation 120 may be emitted at a single energy spectrum or multi-energy spectra depending upon, among other things, whether the CT system is configured as a single-energy CT system or a multi-energy (e.g., dual-energy) CT system.

As the emitted radiation 120 traverses the object 104, the radiation 120 may be attenuated (e.g., absorbed and/or scattered) differently by different aspects of the object 104. Because different aspects attenuate different percentages of the radiation 120, the number of photons detected by respective detector cells of the detector array 118 may vary. For example, detector cells that are shadowed by dense aspects of the object 104, such as a bone or metal plate, may detect fewer radiation photons (while the ratio between high energy radiation photons and low energy radiation photons may be higher) than detector cells that are shadowed by lower density aspects of the object 104, such as skin or clothing, which may allow an overall greater number of radiation photons to pass through and/or may allow a greater number of low energy radiation photons to pass through.

Respective detector cells of the detector array 118 may comprise a radiation conversion element and an electronics arrangement (e.g., DAS). The radiation conversion element is configured to indirectly convert and/or directly convert radiation photons into charge and the electronics arrangement is configured to generate an analog signal and/or to generate information regarding detection events.

The radiation conversion element generally comprises a conversion material and a thin-film transistor (TFT) array configured to detect/accumulate charge generated in response to a detection event. In a direct conversion detector array, the conversion material is configured to convert the radiation photons into electrical charge. Example conversion materials of a direct conversion detector array include, among others, Cadmium Zinc Telluride, Cadmium Telluride, Silicon, and/or an amorphous material. In an indirect conversion detector array, the conversion material is configured to convert the radiation photons into optical light photons, and the radiation conversion element further comprises a photodetector (e.g., a photodiode, such as a back-illuminated photodiode) configured to convert the optical light photons into electrical charge. Example conversion materials of an indirect conversion detector array (also referred to as a scintillator material) include, among others, Cadmium Tungstate, Bismuth Germanate, Cesium Iodide, Sodium Iodide, Gadolinium Oxysulfide and/or Lutetium Orthosilicate.

The electronics arrangement of the detector array 118 is generally configured to convert the electrical charge into a voltage signal and/or process the voltage signal. Such processing may include filtering, shaping, and/or measuring the voltage signal to generate useful information regarding respective detection events on a detector cell. By way of example, in some embodiments, the electronics arrangement comprises an integration circuit configured to generate a voltage signal proportional to the charge produced in response to a detection event and/or a photon counting circuit configured to count and/or tabulate (e.g., record) a number of detection events and/or an energy of respective detection events.

In some embodiments, the electronics arrangement is also configured to compile and/or correct information recorded during a measurement interval (i.e., a view). The information represents the attenuation of radiation through the object while the radiation source 116 and/or detector array 118 were at a particular angular location (or angular range) relative to the object 104.

Information generated and/or compiled by the electronics arrangement may be output to an image generator 122 configured to generate an image(s) of the object 104 using the output of the electronics arrangement. Such images may depict a two dimensional representation of the object 104 and/or a three dimensional representation of the object 104. In other embodiments, the information may be output to other digital processing components, such as a threat analysis component, for processing.

The radiation imaging system 100 also includes a terminal 124, or workstation (e.g., a computer), configured to receive image(s) from the image generator 122, which can be displayed on a monitor 126 to a user 128 (e.g., security personnel, medical personnel, etc.). In this way, the user 128 can inspect the image(s) to identify areas of interest within the object(s) 104. The terminal 124 can also be configured to receive user input which can direct operations of the examination unit 102 (e.g., a speed of gantry rotation, an energy level of the radiation, etc.).

In the radiation imaging system 100, a controller 130 is operably coupled to the terminal 124. The controller 130 may be configured to control operations of the examination unit 102, for example. By way of example, in some embodiments, the controller 130 may be configured to receive information from the terminal 124 and to issue instructions to the examination unit 102 indicative of the received information (e.g., adjust a speed of a conveyor belt, adjust a voltage applied to the radiation source 116, etc.).

Figure 2:
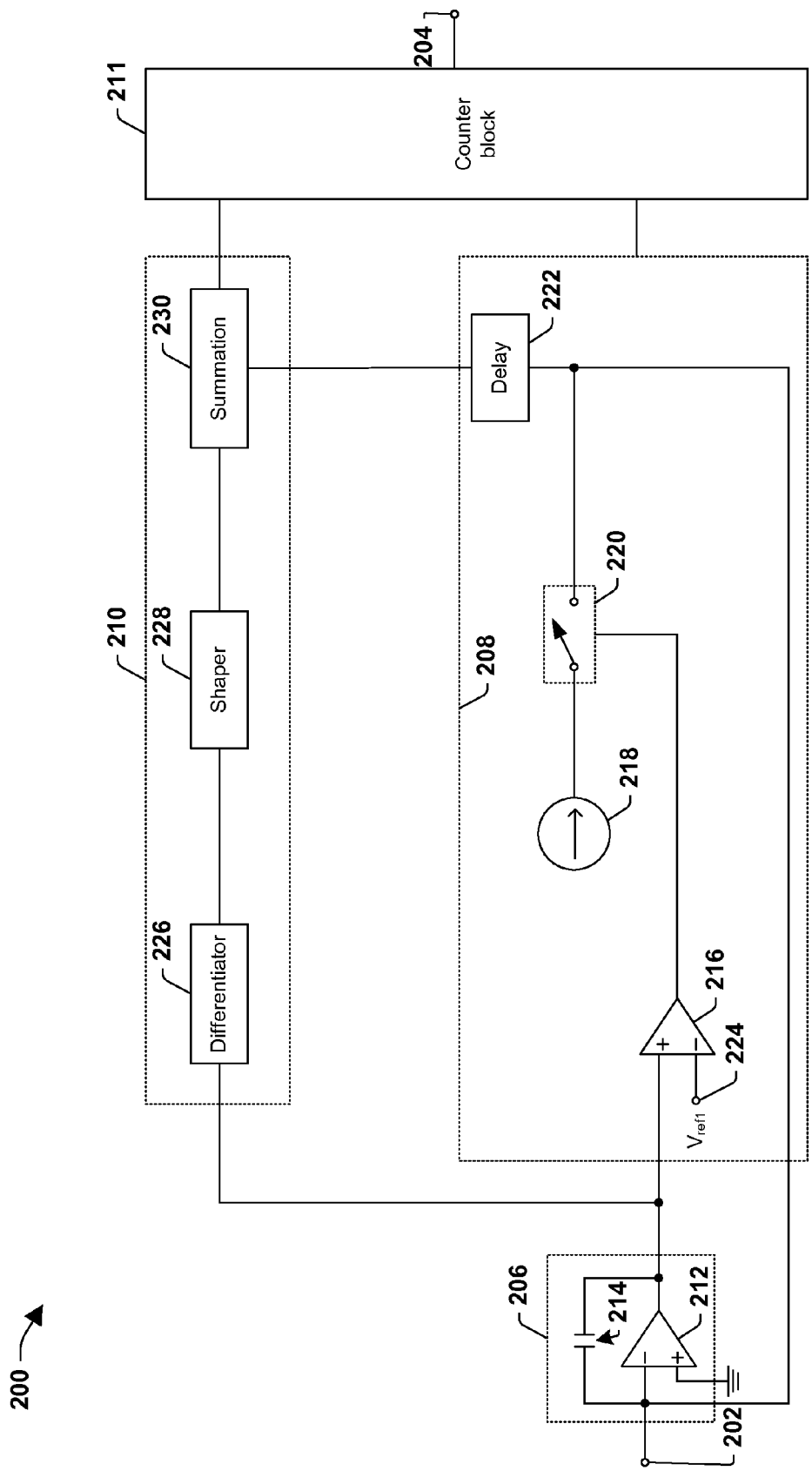
FIG. 2 illustrates a schematic diagram of an example electronics arrangement of a detector cell.

Referring to FIG. 2, a schematic diagram of an example electronics arrangement 200 of a detector cell is illustrated. Additional details regarding at least some of the example electronics arrangement 200 and/or functions details thereof may be found in PCT Patent Application PCT/US13/61713, which is incorporated herein by reference.

When a radiation photon impinges a radiation conversion element, charge is generated within the radiation conversion element, which flows as a pulse of current into the electronics arrangement 200 via a first terminal 202 operably coupled to the radiation conversion element. The amplitude of the pulse is typically indicative of an energy level of the radiation photon. The electronics arrangement is configured to convert the pulse into a voltage signal and to process the voltage signal to generate information about the detection event. Such information may include, among other things, when the detection event occurred and an energy level of the detected radiation photon. The information about various detection events is compiled at counter block 211 (e.g., circuit) configured to determine the number of detection events that occur within a measurement interval, based upon an output from a summation circuit 230 (e.g., to derive photon counting readings or photon counting data) and/or to determine an average number of detection events that occur within a measurement interval based upon an output from a charge injection circuit 208 (e.g., to derive integration readings or integration data). The compiled information is output from the electronics arrangement 200 at a second terminal 204 operably coupled to an image generator (e.g., 122 in FIG. 1) and/or other digital processing component (e.g., a threat analysis component, object identification component, etc.).

The electronics arrangement 200 comprises an integration circuit 206, the charge injection circuit 208, a photon counting circuit 210, and the counter block 211.

The integration circuit 206 (also referred to as a charge amplifier) is configured to convert the pulse into a voltage signal. In some embodiments, the integration circuit 206 comprises an operational-amplifier (op-amp) 212 and a capacitor 214 which are coupled in parallel to create a feedback loop. When a pulse of electrical charge is applied to the op-amp 212, a voltage potential at an input side of the op-amp 212 increases and a voltage potential with an inverse polarity appears at the output side of the op-amp 212. The voltage potential at the output side of the op-amp 212 is fed through the feedback loop, causing the voltage potential at the input-side to return to zero (e.g., nearly instantaneously) and/or causing the pulse to be integrated into a feedback capacitance of the capacitor 214. Such integration causes a voltage signal to be output from the integration circuit 206 that is substantially proportional to the charge received at the first terminal 202.

As radiation photons continue to be detected by the radiation conversion element and converted to charge, the amplitude of the voltage signal may increase to an undesirable level (e.g., a level that may introduce a substantial amount of error) due to the accumulation of stored charge at the capacitor 214. Accordingly, the charge injection circuit 208 is configured to inject charge into the integration circuit 206 when the voltage signal exceeds a specified threshold. The injected charge is typically opposite in polarity to the stored charge at the capacitor 214 and is configured to reset the integration circuit 206 by reducing (i.e., counteracting) an amount of stored charge at the capacitor 214. In this way, by resetting the integration circuit 206, an amplitude (magnitude) of the voltage signal output by the integration circuit 206 may be intermittently and/or periodically reduced (e.g., to limit a number of photons detected per reset, reduce noise in the electronics arrangement 200, etc.), for example. In some embodiments, a reset indication is applied to the counter block 211 when a reset is performed. In this way, the counter block 211 may count the number of resets per view to supplement information obtained from summation circuit 230, for example.

The charge injection circuit 208 comprises a comparator 216 (e.g., an op-amp), a charge source 218, a switching element 220, and a delay circuit 222. The comparator 216 is configured to compare the voltage signal output by the integration circuit 206 to a reference voltage signal associated with the specified threshold and applied at a terminal 224. When the comparator 216 senses that the voltage signal output by the integration circuit 206 exceeds the reference voltage signal (thus exceeding the specified threshold), the comparator 216 is configured to generate a first switch signal configured to activate the switching element 220 (causing the charge source 218 to be electrically coupled to the integration circuit 206). In some embodiments, the switching element 220 is configured to be activated for a specified period of time that causes a specified amount of charge to be injected into the integration circuit 206. In some embodiments, the number of resets that occur within a measurement interval is proportional to the average current generated in response to detector events within the measurement interval. For example, in some embodiments, the average current is equal to the number of resets multiplied by the amount of charge to be injected during each reset divided by the measurement interval. In some embodiments, the average current may be referred to as an integrator reading. Moreover, in some embodiments, the measurement interval is equal to a view and the number of resets that occur within the measurement interval is counted to yield the approximate number of photons detected by the detector cell during a view.

The charge source 218 is configured to generate charge that will reduce the stored charge at the capacitor 214. For example, the charge source 218 is configured to inject charge into the integration circuit 206 when the charge source 218 is electrically coupled to the integration circuit 206. The injected charge is opposite in polarity to the stored charge and, in some embodiments, is proportional to the stored charge. For example, in some embodiments, the injected charge is inversely matched to the stored charge to reduce the amount of stored charge at the capacitor 214 to substantially zero or another predetermined amount.

In some embodiments, the specified threshold (and thus the reference voltage signal) is selected to achieve a desired noise level for integration readings in counter block 211, which are derived from an output of the charge injection circuit 208. By way of example, in some embodiments, it is desirable that errors in an image (which may be manifested as artifacts in the image) be limited to errors due to quantum noise of the photons being measured (inherent in photon counting). Accordingly, in such embodiments, the specified threshold is selected to provide that a noise power introduced by the integration reading derived from the charge injection circuit 208 is less than the noise power of the quantum noise at a particular photon rate. That is, stated differently, the specified threshold is selected as a function of a signal-to-noise ratio of the photon counting circuit 210 at a particular photon rate.

Moreover, in some embodiments, the specified threshold and/or the injected charge is a function of an energy spectrum of radiation photons emitted by the radiation source and/or a function of a source voltage applied to a radiation source (e.g., 116 in FIG. 1) configured to expose the photon counting detector array (e.g., 118 in FIG. 1) to radiation. By way of example, the amount of charge injected into the capacitor 214 via the charge source 218 may differ depending upon whether an average energy of emitted radiation photons is 60 keV or 100 keV. As another example, a first specified threshold may be defined for the voltage signal when 120 kVp is applied to the radiation source and a second specified threshold, different than the first specified threshold, may be defined for the voltage signal when 150 kVp is applied to the radiation source. Moreover, the specified threshold and/or the amount of charge injected into the capacitor 214 may vary during an examination of an object (e.g., 104 in FIG. 1) if the average energy of emitted radiation photons changes during the examination and/or the source voltage applied to the radiation source changes during the examination. By way of example, the source voltage applied to the radiation source (and the average energy of emitted radiation photons) may vary as the radiation source is rotated from viewing a side of a torso to a front of the torso. In some embodiments, concurrently with varying the source voltage during the rotation, the specified threshold and/or the output of the charge source 218 may be varied (e.g., proportionally with the change to the source voltage).

The switching element 220 is configured to be activated or deactivated as a function of the switch signal output by the comparator 216 (which is directly or indirectly coupled to the switching element 220). While the switching element 220 is activated (i.e., the switch is closed), the charge source 218 is electrically coupled to the integration circuit 206 and charge is injected into the integration circuit 206 via the charge source 218. The switching element 220 may comprise one or more suitable electronic switches such as insulated gate bipolar transistors (IGBTs), bipolar junction transistors (BJTs), field-effect transistors (FETs), metal-oxide semiconductor field-effect transistors (MOSFETs), gate turnoff thyristors (GTOs), integrated gate-commutated thyristors (IGCTs), and/or bidirectional triode thyristors (TRIACs), for example. In some embodiments, the switching of the switching element 220 may be a function of the comparator 216, and may not necessarily be directly connected to the comparator 216.

It may be appreciated that in some embodiments, charge generated at the radiation conversion element may be applied to the integration circuit 206 concurrently with the injected charge being applied to the integration circuit 206. To distinguish the impact of the injected charge on the voltage signal from the impact of the charge generated at the radiation conversion element, the injected charge may be further injected into the photon counting circuit 210 or a summation circuit 230 thereof. In this way, the photon counting circuit 210 and/or summation circuit 230 can differentiate the impact of the injected charge from the impact of the charge indicative of one or more detection events (e.g., to facilitate the counting of detection events that occur concurrently with the resetting of the integration circuit 206).

It some embodiments, it is desirable for the injected charge to be injected into the summation circuit 230 concurrently with a voltage signal indicative of the injected charge (e.g., yielded from the integration circuit 206). Accordingly, the charge injection circuit 208 comprises a delay circuit 222 configured to delay an application of the injected charge to the summation circuit 230 until a signal, yielded from the integration circuit 206 and indicative of the injected charge, is also applied to the summation circuit 230, for example.

The photon counting circuit 210 is configured to identify detection events and/or determine an energy level of respective detection events as a function of the voltage signal generated by the integration circuit 206. In this way, a record of detection events experienced by the detector cell is generated. The photon counting circuit 210 comprises a differentiator circuit 226, a shaper circuit 228, and the summation circuit 230. The differentiator circuit 226 is configured to generate a second voltage signal that is proportional to a rate of change of the voltage signal output by the integration circuit 206. Thus, an amplitude of the second voltage signal may be greater when the voltage signal output by the integration circuit 206 experiences a fast rate of change (e.g., when the voltage drops from 1.5 V to 1 V in 2 ns) than when the voltage signal output by the integration circuit 206 experiences a slower rate of change (e.g., when the voltage drops from 1.5 V to 1 V in 5 ns), for example.

The shaper circuit 228, such as a low-pass filter or other filter, is configured to shape the second voltage signal to generate a shaper signal. In this way, the second voltage signal may be smoothed, amplified, and/or otherwise adjusted to prepare the second voltage signal for the summation circuit 230.

The summation circuit 230 is configured to sum the shaper signal with the signal output from the delay circuit 222 or an equivalent thereof (e.g., indicative of the injected charge) to generate a signal (e.g., a voltage signal and/or a current signal). Respective pulses in the signal are indicative of a detection event and the magnitude of a pulse is indicative of an energy associated with the detection event (e.g., energy of the detected photon). Moreover, by summing the shaper signal with the signal output from the delay circuit 222, detection events that occur substantially concurrently with the injection of charge into the integration circuit 206 can be identified. That is, stated differently, the summation can cause the impact of the injected charge on a voltage pulse emitted from the integration circuit 206 to be removed such that the signal output from the summation circuit 230 is merely indicative of detection events (e.g., and not indicative of injected charge), for example.

The counter block 211 is configured to generate data indicative of detection events based upon the signal output by the summation circuit 230 and the signal output by the charge injection circuit 208. The data may include photon counting data and integration data. Photon counting data refers to data generated based upon the signal output by the summation circuit 230 and may be indicative of photon counting readings (which may include a detection time and detection location of respective detection events). Integration data refers to data generated based upon the signal output by the charge injection circuit 208 and may be indicative of integration readings (which may include an amount of time between respective resets). In some embodiments, the counter block 211 is configured to determine a number of detection events that occur per measurement interval (i.e., per view) based upon the photon counting data and/or the integration data.

In some embodiments, the data output by the counter block 211 and used for imaging purposes (e.g., to generate an image) may be based upon the number of detection events identified within a measurement interval (i.e., a view). By way of example, when the number of detection events identified during a measurement interval is less than a first detection event count threshold (e.g., as determined based upon the number of pulses in the signal output by the summation circuit 230 during the measurement interval and/or the number of resets by the charge injection circuit 208 during the measurement interval), the photon counting data may be output from the counter block 211 to represent the measurement interval (and thus photon counting data is used for imaging purposes). When the number of detection events identified during a measurement interval exceeds a second detection event count threshold, the integration data may be output from the counter block 211 to represent the measurement interval (and thus integration data is used for imaging purposes). When the number of detection events identified during a measurement interval is between the first detection event count threshold and the second detection event count threshold, the integration data may be blended with the photon counting data to generate a blended output representing the measurement interval. In this way, imaging data may be generated based upon the number of detection events that occur within a measurement interval using photon counting techniques (i.e., photon counting readings) and/or the effective or average number of detection events using integration techniques (i.e., photon integration readings).

Figure 3:
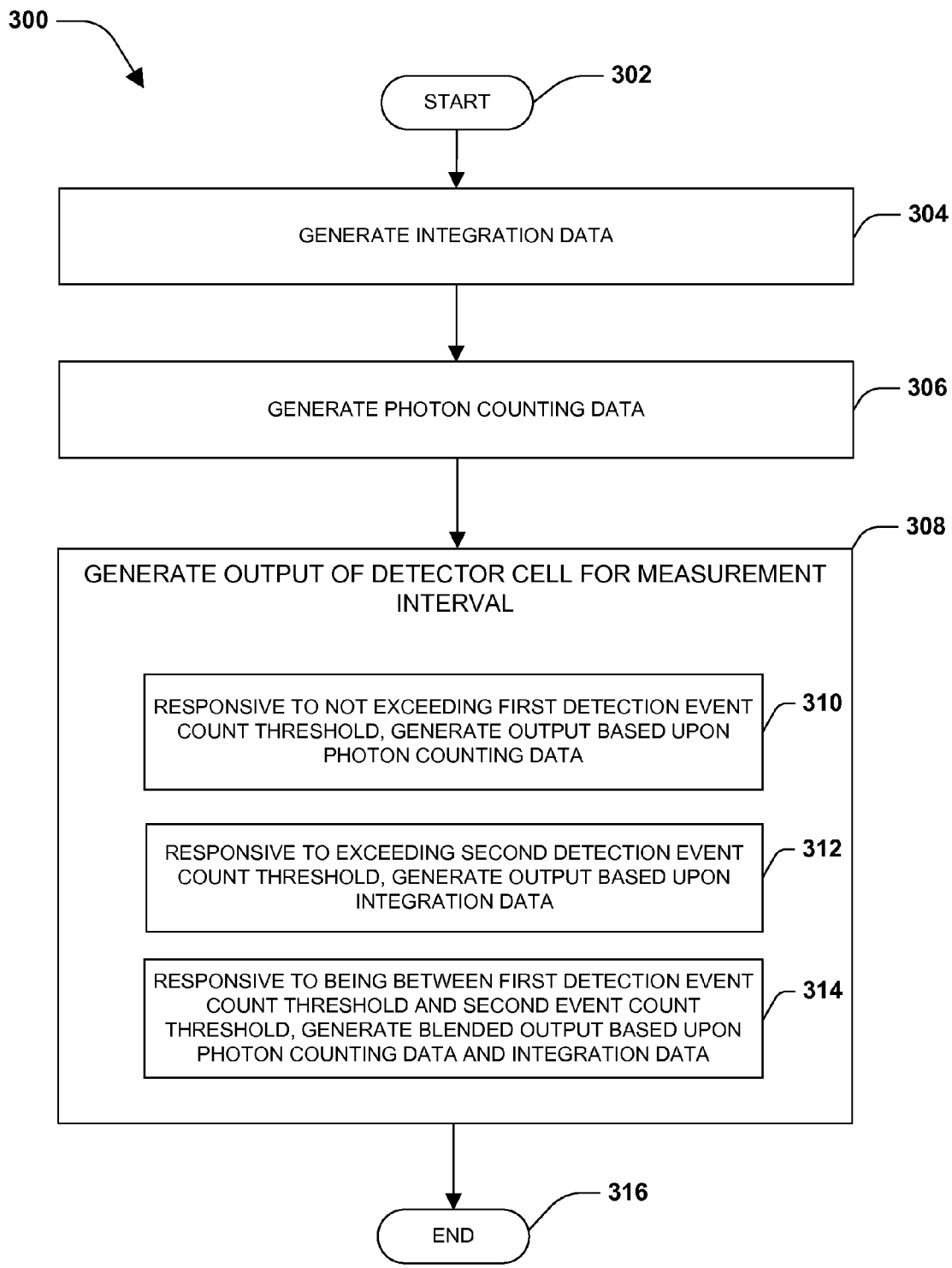
FIG. 3 is a flow diagram illustrating an example method for determining an output for a detector cell of a photon counting detector array.

Referring to FIG. 3, a flow diagram of an example method 300 for determining an output (of the counter block 211) for a detector cell of the photon counting detector array 118 is provided. The output is indicative of the number and/or energy of radiation photons detected by the detector cell during a measurement interval and may be based upon the photon counting data and/or the integration data.

The example method 300 starts at 302. At 304, integration data is generated based upon a number of resets to the integration circuit 206 during the measurement interval. The number of resets occurring within the measurement interval is equivalent to the number of instances in which the charge injection circuit 208 injected charge into the integration circuit 206 during the measurement interval. For example, when the charge injection circuit 208 injects charge into the integration circuit 206, the charge injection circuit 208 may generate a signal pulse, which is provided to the counter block 211. The counter block 211 may tabulate the number of signal pulses received during the measurement interval to determine the number of resets to the integration circuit 206 during the measurement interval. The counter block 211 may use this number and the voltage of the voltage reference signal, for example, to generate the integration data (approximating a number of photons detected during the measurement interval). The integration data is indicative of an integration of energy collected by the photon counting detector array 118 or by the detector cell of the photon counting detector array 118 during the measurement interval of the radiation imaging system 100.

At 306 in the example method 300, photon counting data is generated based upon a signal received from the photon counting circuit 210 or a summation circuit 230 thereof. The photon counting data may be indicative of a number of photons counted by the photon counting detector array 118 or the detector cell of the photon counting detector array 118 during the measurement interval. In some embodiments, the photon counting data is also indicative of an energy of respective detection events.

In some embodiments, for respective measurement intervals or views, the counter block 211 is configured to output data indicative of measurements acquired during the measurement interval (e.g., and thus indicative of the number of photons counted/approximated during the measurement interval). To determine whether to output the photon counting data, integration data, or a combination of the photon counting data and the integration data for a measurement interval, a first detection event count threshold and a second detection event count threshold are defined.

In an example, as will be further described with respect to FIG. 4, the first detection event count threshold may be defined based upon an error and/or noise curve associated with the photon counting circuit 210. The first detection event count threshold may comprise a first detection event count value (e.g., 400 detection events/measurement interval) corresponding to a point on the error and/or noise curve where error and/or noise of photon counting data derived from the photon counting circuit 210 exceeds a first threshold indicative of an unacceptable level of noisy and/or erroneous photon counting data (e.g., the photon counting data may become inaccurate, such as noisy and/or erroneous, when the photon counting circuit 210 attempts to count a number of photons exceeding the first detection event count value). The first detection event count threshold may be based upon a temporal length of the measurement interval, conversion materials of the radiation conversion element, properties of the electronic elements of the electronics arrangement 200, etc.

In an example, as will be further described with respect to FIG. 4, the second detection event count threshold may be defined based upon an error and/or noise curve associated with the integration circuit 206 and/or the charge injection circuit 208. The second detection event count threshold may comprise a second detection event count value (e.g., 600 detection events) corresponding to a point on the error and/or noise curve where error and/or noise of integration data derived from the integration circuit 206 and/or charge injection circuit 208 exceeds a second threshold indicative of an unacceptable level of noisy and/or erroneous integration data (e.g., the integration data may be inaccurate, such as noisy and/or erroneous, for numbers of detection events that do not exceed the second detection event count value, but may have a desired quality for numbers of detection events exceeding the second detection event count value). The second detection event count threshold may also be based upon a temporal length of the measurement interval, conversion materials of the radiation conversion element, properties of the electronic elements of the electronics arrangement 200, etc.

At 308, an output of the detector cell, or an electronics arrangement thereof, is generated for the measurement interval. The output of the detector cell may be a function of the number of photons identified during the measurement interval, the first detection event count threshold, and/or the second detection event count threshold.

For example, responsive to the number of detection events not exceeding the first detection event count threshold for the measurement interval, the counter block 211 may generate a first output for the measurement interval at 310. The first output may be based upon (e.g., indicative of) the photon counting data, but not the integration data, because the photon counting data may be less noisy and/or erroneous compared to the integration data for photon counts above the second detection event count threshold. Responsive to the number of detection events exceeding the second detection event count threshold for the measurement interval, the counter block 211 may generate a second output for the measurement interval at 312. The second output may be based upon the integration data, but not the photon counting data, because integration data may be less noisy and/or erroneous compared to the photon counting data for photon counts above the second detection event count threshold (e.g., noise and/or errors may occur when counting such a relatively large number of photons, and thus data yielded from energy integration may provide better quality information than data yielded from photon counting).

At 314, responsive to the number of detection events being between the first detection event count threshold and the second detection event count threshold for the measurement interval, a blended output may be generated. The blended output may be based upon the photon counting data and the integration data. Because the blended output is based upon both the photon counting data and the integration data, the blended output may reduce imaging artifacts otherwise introduced by the discontinuity between the integration data and the photon counting data, for example.

Expressed as an equation, element 308 (i.e., 310-314) of the example method 300 may be represented as:

$$S_{blend} = \begin{cases} S_{SPC}, & \text{low count region} \\ wS_{CI} + (1-w)S_{SPC}, & \text{crossover region} \\ S_{CI}, & \text{high count region} \end{cases} \quad (1)$$

where $S_{blend}$ corresponds to the output of the detector cell or rather the output of the electronics arrangement 200 (e.g., at the second terminal 204); $S_{SPC}$ corresponds to the photon counting data; low count region corresponds to a number of detection events less than or equal to the first detection event count threshold; $S_{CI}$ corresponds to the integration data; w corresponds to a first blending weight applied to the integration data; (1−w) corresponds to a second blending weight applied to the photon counting data; crossover region corresponds to a number of detection events being between the first detection event count threshold and the second detection event count threshold; and high count region corresponds to a number of detection events greater than or equal to the second detection event count threshold.

Various blending techniques may be used to blend the photon counting data and the integration data. That is, stated differently, various techniques may be used to determine the first blending weight (corresponding to w in equation 1) and the second blending weight (corresponding to (1−w) in equation 1) that are applied to the integration data and photon counting data, respectively, to determine how to blend the photon counting data with the integration data to generate the blended output. In an example, the first blending weight and the second blending weight may be derived using a linear interpolation blending function. The linear interpolation blending function may be expressed as:

$$w(x)=x \quad (2)$$

where x corresponds to a normalized crossover region coordinate. For example, x may correspond to 0 at the first detection event count threshold and may correspond to 1 at the second detection event count threshold. The value of x can be calculated as a ratio of a difference between the number of detection events identified during the measurement interval and the first detection event count threshold to a difference between the second detection event count threshold and the first detection even count threshold.

As another example, the first blending weight and the second blending weight may be derived using a first-derivative matching blending function which results in a continuous value of the corrected data and a continuous value of the first derivative of corrected data at the end points of the crossover region. One example of such first-derivative matching function is $$w(x)=3x^2-2x^3 \quad (3)$$

where x=(T(2)−S)/(T(2)−T(1)). In some embodiments, T(1) corresponds to the first detection event count threshold, T(2) corresponds to the second detection event count threshold, and S corresponds to a measured signal.

As another example, the first blending weight and the second blending weight may be derived based upon both a signal to noise and error ratio (SNER) for the integration data and a SNER for the photon counting data. Depending on the shape of a noise and/or error curve associated with the photon counting circuit 210 and/or the shape of a noise and/or error curve associated with the integration circuit 206, the first blending weight and/or the second blending weight can be refined to achieve a desired (e.g., optimum) signal to noise and/or error ratio across the crossover region. Within the crossover region represented by equation 1, the signal to noise and/or error ratio of the blended signal may be expressed as:

$$SNER_{blend} = \frac{(1-w)S_{SPC} + wS_{CI}}{\sqrt{(1-w)^2(\sigma_{SPC}^2 + \varepsilon_{SPC}^2) + w^2(\sigma_E^2 + \sigma_{CI}^2 + \varepsilon_{CI}^2)}} \quad (4)$$

where $\sigma_{SPC}^2$ corresponds to quantum noise variance of the photon counting data; $\epsilon_{SPC}^2$ corresponds to a squared photon counting data error; $\sigma_E$ corresponds to electronic noise of the integration circuit 206; $\sigma_{CI}^2$ corresponds to quantum noise variance of the integration data; and $\epsilon_{CI}^2$ corresponds to a squared integration data error.

In some embodiments, prior to applying the first blending weight to the integration data and/or applying the second blending weight to the photon counting data, a scaling factor is applied to at least one of the integration data or the photon counting data. The scaling factor is configured to normalize the integration data with respect to the photon counting data. In some example, application of the scaling factor may be expressed as:

$$S_{CI} = \frac{C_{CI}}{k} \quad (5)$$

where $S_{CI}$ corresponds to the integration data after scaling; $C_{CI}$ corresponds to the integration data prior to scaling; and k corresponds to the scaling factor. In some embodiments, the scaling factor, k, may be expressed as:

$$k = \xi E_{mean} e \frac{C_{max}}{Q_{max}} \quad (6)$$

where $\xi$ is a conversion factor of the radiation conversion element (e.g., in electrons/keV); $E_{mean}$ is the mean photon energy of emitted radiation (e.g., in keV); e is an electron charge (e.g., in Coulombs); $C_{max}$ is a full scale count of the integrator circuit 206; and $Q_{max}$ is a full scale integrator charge (e.g., in Coulombs).

The example method 300 ends at 316.

FIG. 4 illustrates an example graph 400 depicting the error associated with photon counting and energy integration as a function of a number of photons detected by a detector cell of a photon counting detector array 118. The y-axis 402 represents an amount of error associated with the data and the x-axis 404 represents a number of photons detected during a measurement interval. A first line 412 within the graph 400 represents an amount of error associated with energy integration and a second line 414 represents an amount of error associated with photon counting. The intersection of the first line 412 and the second line 414 defines a crossover point 416. If the number of photons detected is less than the crossover point 416, the magnitude of error in photon counting data is smaller than the error in integration data. If the number of photons detected is greater than the crossover point 416, the magnitude of error in photon counting data is greater than the error in integration data.

A crossover region 410 may be defined based upon the crossover point 416. For example, the crossover region 410 may be defined to be +/−a particular number of photons away from the crossover point 416. A lower boundary 418, representative of the first detection event count threshold, is a defined first distance (e.g., in terms of number of photons) from the crossover point 416 and defines an upper boundary of a low count region 406 where the photon counting data is used for image generation and the integration data is not used. An upper boundary 420, representative of a second detection event count threshold, is a defined second distance (e.g., in terms of number of photons) from the crossover point 416 and defines a lower boundary of a high count region 408 where the integration data is used for image generation and the photon counting data is not used. In some embodiments, the defined first distance is equal to the defined second distance. In other embodiments, the defined first distance may be different than the defined second distance. The crossover region 410 may be defined between the lower boundary 418 and the upper boundary 420. For photon counts within the crossover region 410, the photon counting data and the integration data may be blended to generate a blended output for use by the image generator 122, for example.

FIGS. 5A-5D illustrate examples of an electronics arrangement 500 of a photon counting detector array. The electronics arrangement 500 comprises a counter block 211. The counter block 211 is configured to perform detection event count threshold evaluations of detection event data. The counter block 211 may define a first detection event count threshold 518 (e.g., 800 detection events per measurement interval) and a second detection event count threshold 520 (e.g., 900 detection events per measurement interval), such as based upon error and/or noise curves of the integration circuit 206, the charge injection circuit 208, and/or the photon counting circuit 210. The first detection event count threshold 518 may indicate that numbers of detection events that do not exceed the first detection event count threshold 518 (e.g., 800 detection events), such as within a low count region 512, may be adequately represented by photon counting data (e.g., in comparison to using integration data). The second detection event count threshold 520 may indicate that numbers of detection events above the second detection event count threshold 520 (e.g., 900 detection events), such as within a high count region 516, may be adequately represented by integration data (e.g., in comparison to using photon counting data). A crossover region 514 may correspond to numbers of detection events between the first detection event count threshold 518 and the second detection event count threshold 520, where merely using the integration data or merely using the photon counting data may otherwise result in imaging artifacts. Accordingly, the counter block 211 may be configured to generate blended outputs from the integration data and the photon counting data for numbers of detection events within the crossover region 514.

Figure 5A:
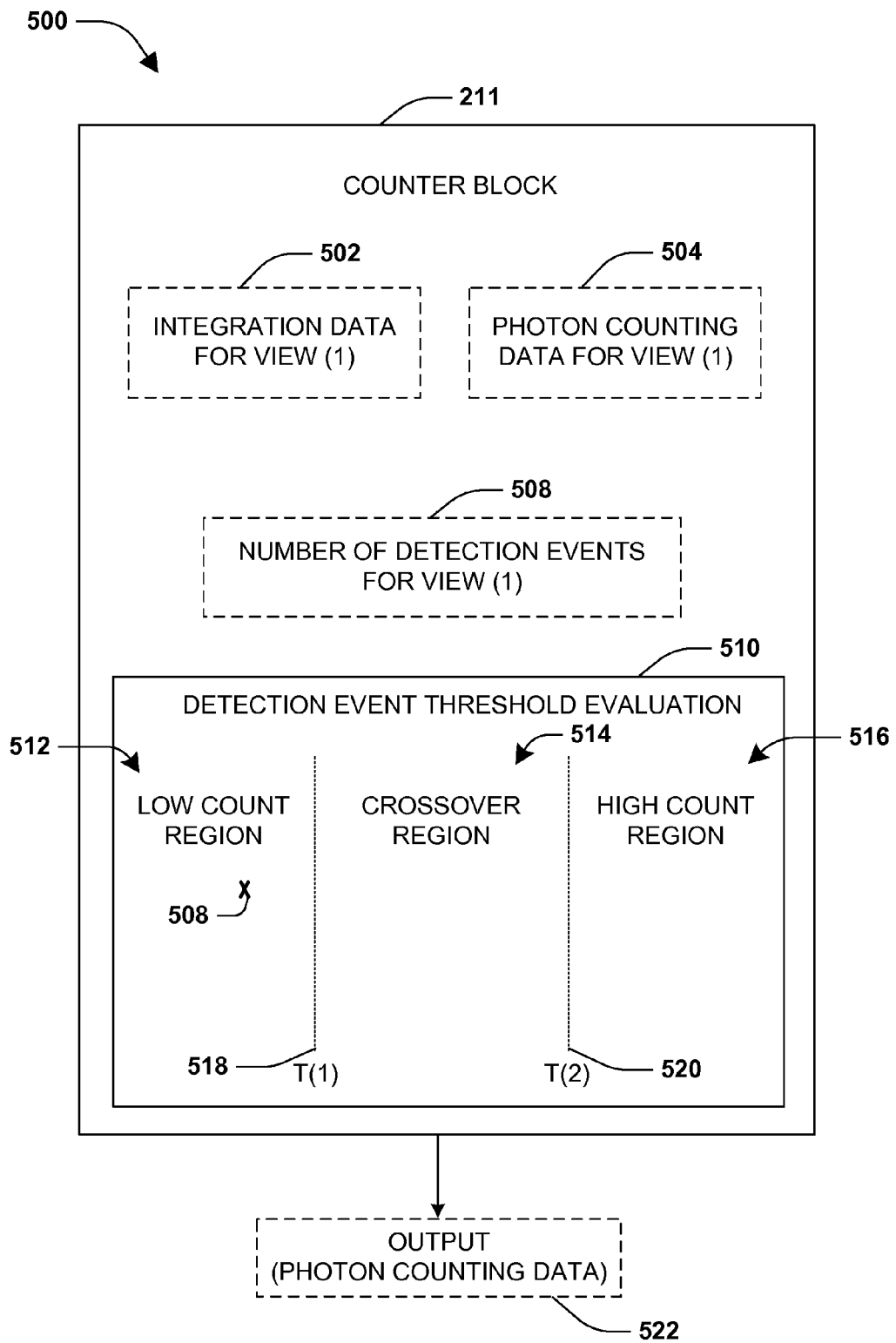
FIG. 5A illustrates an example output associated with a photon counting detector array, where the output corresponds to photon counting data.

FIG. 5A illustrates the counter block 211 generating integration data 502 and/or photon counting data 504 for a view (1) that is being captured by a radiation imaging system comprising the electronics arrangement 500. The counter block 211 may determine 510 that a number of detection events 508 for view (1) (e.g., 530 detection events) may correspond the low count region 512 that is less than the first detection event count threshold 518. Because the photon counting circuit 210 may provide relatively accurate (e.g., low noise and/or error) photon counting data 504 compared to the integration data 502 due to the photon counting circuit 210 counting individual photons, the counter block 211 may generate an output 522 for the view (1) based upon the photon counting data 504. Thus, the image generator 122 uses the photon counting data 504, but not the integration data 502, when processing the data for view (1).

Figure 5B:
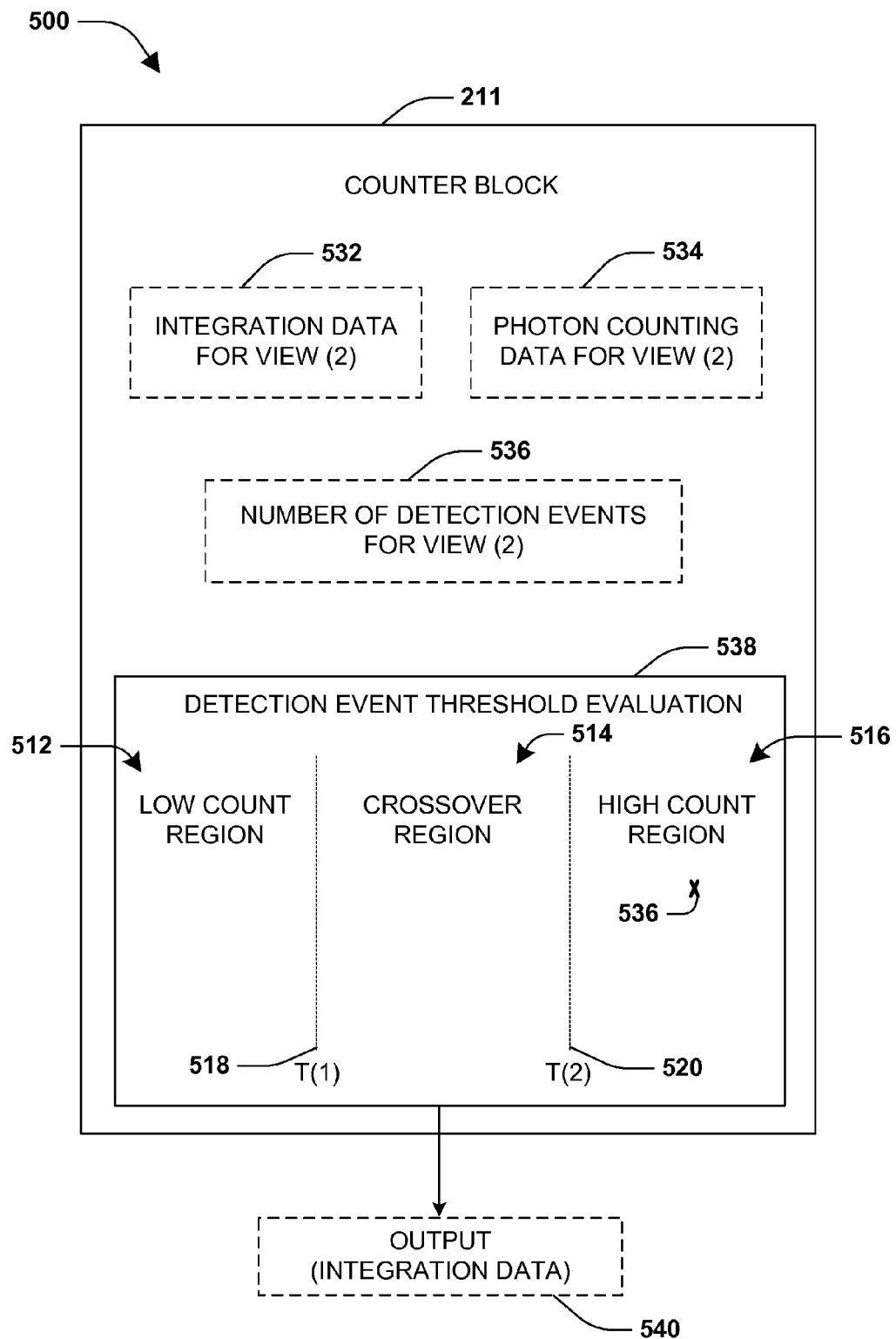
FIG. 5B illustrates an example output associated with a photon counting detector array, where the output corresponds to integration data.

FIG. 5B illustrates the counter block 211 generating integration data 532 and/or photon counting data 534 for a view (2) that is being captured by the radiation imaging system. The counter block 211 may determine 538 that a number of detection events 536 for view (2) (e.g., 1,250 detection events) may correspond to the high count region 516 that is greater than the second detection event count threshold 520. Because the integration circuit 206 may provide relatively accurate (e.g., low noise and/or error)

integration data 532 compared to the photon counting data 534 due to the integration circuit 206 integrating energy of photons (e.g., whereas the photon counting circuit 210 may be have a greater error due to saturation phenomenon associated with a larger number of detection events are occurring during the view (2)), the counter block 211 may generate an output 540 for the view (2) based upon the integration data 532. Thus, the image generator 122 uses the integration data 532, but not the photon counting data 534, when processing the data for view (2).

Figure 5C:
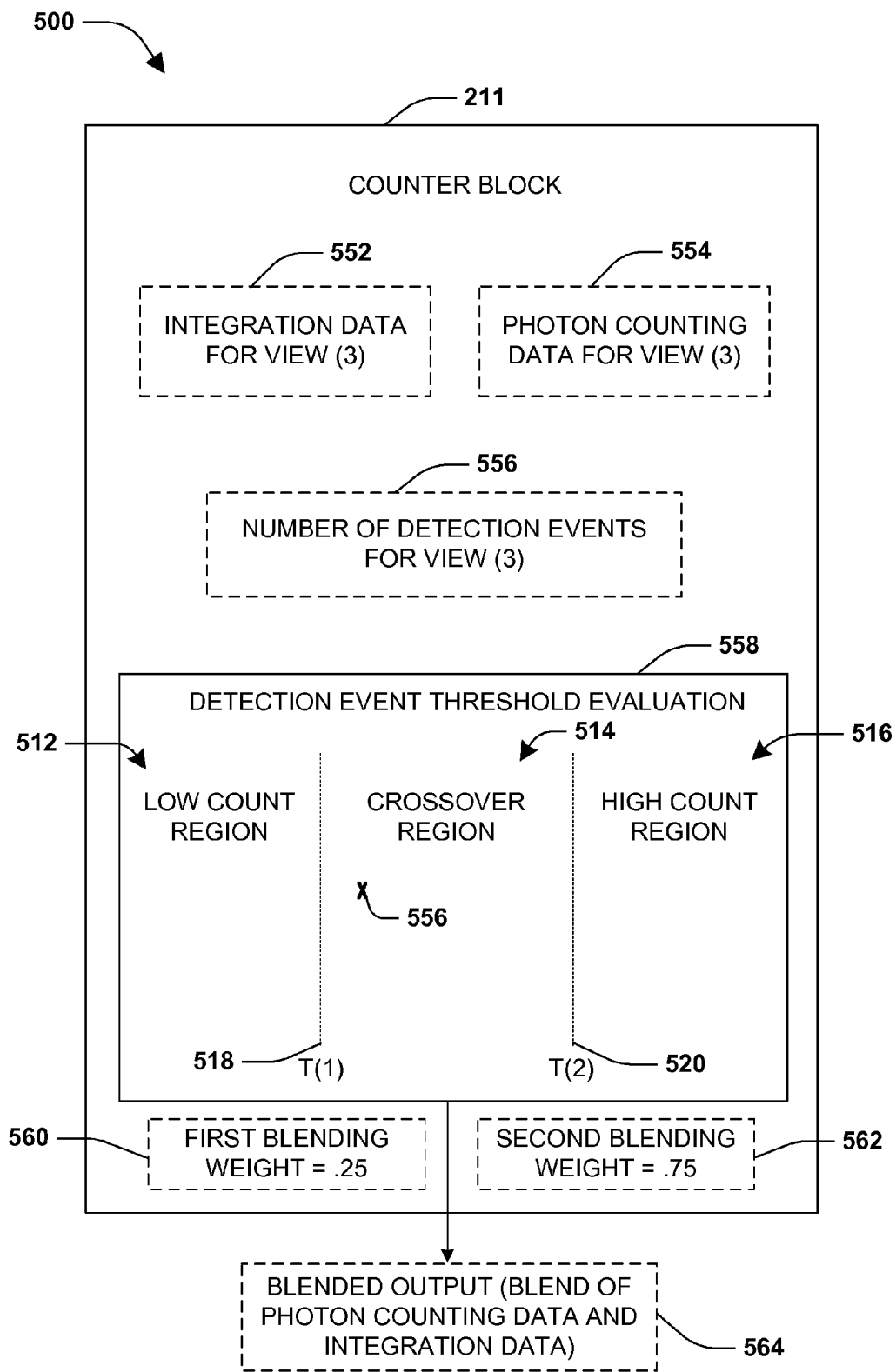
FIG. 5C illustrates an example blended output associated with a photon counting detector array, where the blended output corresponds to integration data and photon counting data.

FIG. 5C illustrates the counter block 211 generating integration data 552 and/or photon counting data 554 for a view (3) that is being captured by the radiation imaging system. The counter block 211 may determine 558 that a number of detection events 556 for view (3) (e.g., 825 detection events) may correspond the crossover region 514 between the first detection event count threshold 518 and the second detection event count threshold 520. The counter block 211 may utilize a blending function, such as the linear interpolation blending function, the first-derivative matching blending function, and/or any other blending algorithm, to generate a blended output 564 based upon the integration data 552 and the photon counting data 554. For example, a first blending weight 560 of 0.25 (e.g., (825–800)/(900–800)) may be determined for integration data 552 and a second blending weight 562 of 0.75 (e.g., 1 minus the first blending weight) may be determined for the photon counting data 554 due to the number of detection events 556 being closer to the low count region 512 than the high count region 516. That is, because the number of detection events 556 for view (3) may be closer to the first detection event count threshold 518 than to the second detection event count threshold 520, the second blending weight 562 (applied to the photon counting data 554) is greater than the first blending weight 560 (e.g., applied to the integration data 552), and thus the photon counting data 554 may contribute more to the blended output 564 than the integration data 552.

Figure 5D:
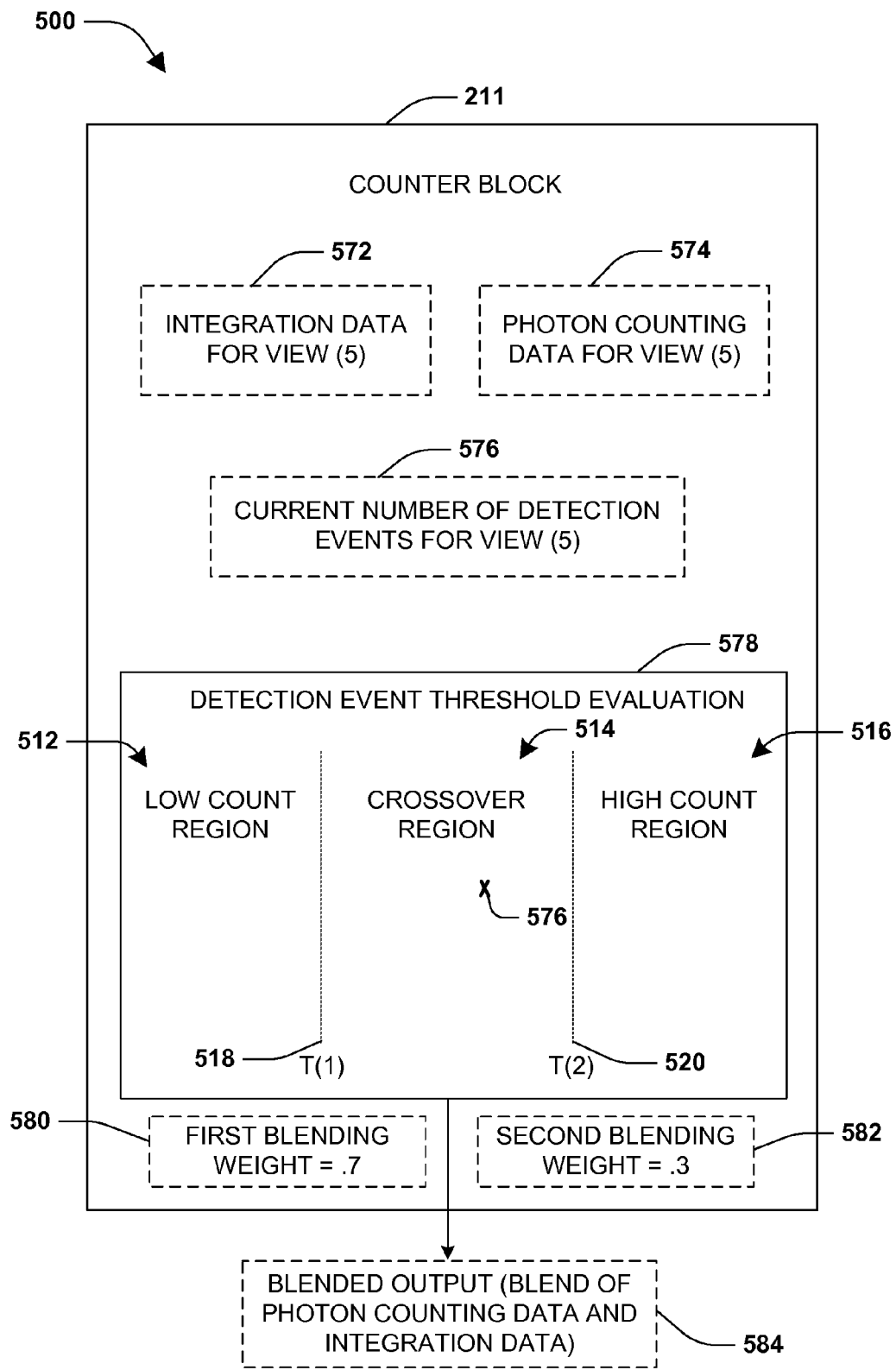
FIG. 5D illustrates an example blended output associated with a photon counting detector array, where the blended output corresponds to integration data and photon counting data.

FIG. 5D illustrates the counter block 211 generating integration data 572 and/or photon counting data 574 for a view (4) that is being captured by the radiation imaging system. The counter block 211 may determine 578 that a number of detection events 576 for view (4) (e.g., 870 detection events) may correspond the crossover region 514 between the first detection event count threshold 518 and the second detection event count threshold 520. The counter block 211 may utilize a blending function, such as the linear interpolation blending function, the first-derivative matching blending function, or any other blending algorithm, to generate a blended output 584 based upon the integration data 572 and the photon counting data 574. For example, a first blending weight 580 of 0.7 (e.g., (870–800)/(900–800)) may be determined for the integration data 572 and a second blending weight 582 of 0.3 (e.g., 1 minus the first blending weight) may be determined for the photon counting data 574 due to the number of detection events 576 being closer to the high count region 516 than the low count region 512. Because the number of detection events 576 for view (4) may be closer to the second detection event count threshold 520 than to the first detection event count threshold 518, the first blending weight 580 (e.g., applied to the integration data 572) is greater than the second blending weight 582 (e.g., applied to the photon counting data), and thus the integration data 572 may contribute more to the blended output 584 than the photon counting data 574.

Figure 6:
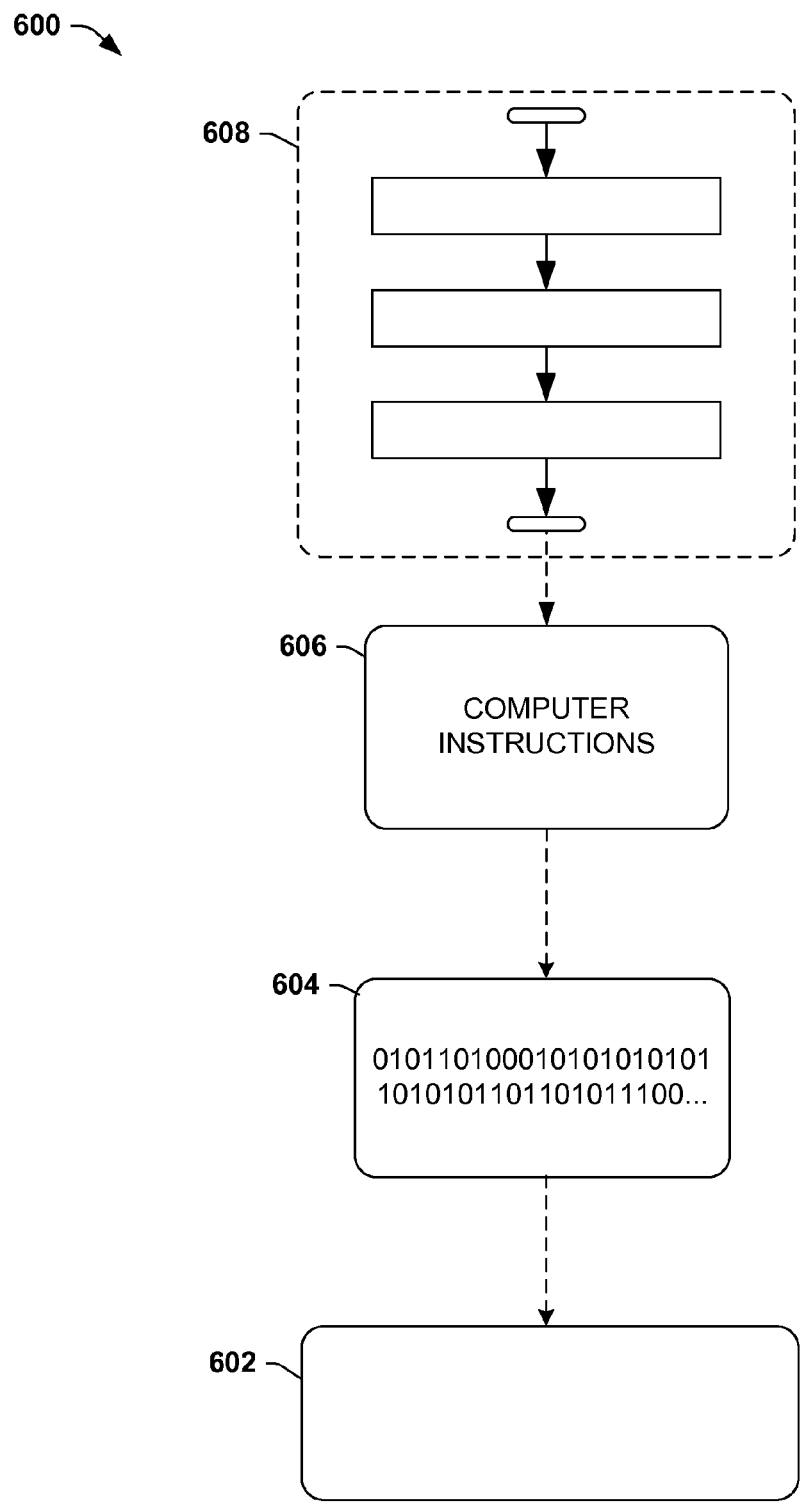
FIG. 6 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 6, wherein the implementation 600 comprises a computer-readable medium 602 (e.g., a flash drive, CD-R, DVD-R, application-specific integrated circuit (ASIC), field-programmable gate array (FPGA), a platter of a hard disk drive, etc.), on which is encoded computer-readable data 604. This computer-readable data 604 in turn comprises a set of processor-executable instructions 606 configured to operate according to one or more of the principles set forth herein. In one such embodiment 600, the processor-executable instructions 606 may be configured to perform a method 608 when executed via a processing unit, such as at least some of the example method 300 of FIG. 3. In another such embodiment, the processor-executable instructions 606 may be configured to implement a system, such as at least some of the example system 100 of FIG. 1. Many such computer-readable media may be devised by those of ordinary skill in the art that are configured to operate in accordance with one or more of the techniques presented herein. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". The claimed subject matter may be implemented as a method, apparatus, or article of manufacture (e.g., as software, firmware, hardware, or any combination thereof).

As used in this application, the terms "component," "module", "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. An electronics arrangement of a photon counting detector array, comprising:
   an integration circuit configured to integrate charge generated by a detector cell of the photon counting detector array to generate a voltage signal;
   a charge injection circuit configured to inject a charge into the integration circuit in response to the voltage signal exceeding a specified threshold, the injected charge configured to reset the integration circuit;
   a photon counting circuit configured to identify detection events based upon the voltage signal; and
   a counter block configured to:
      generate integration data indicative of an amount of charge integrated by the integration circuit during a measurement interval based upon a number of resets to the integration circuit during the measurement interval;
      generate photon counting data indicative of a number of detection events identified by the photon counting circuit during the measurement interval; and
      responsive to the number of detection events being between a first detection event count threshold and a second detection event count threshold for the measurement interval:
         apply a first blending weight to the integration data to create weighted integration data;
         apply a second blending weight to the photon counting data to create weighted photon counting data; and
         generate a blended output based upon the weighted integration data and the weighted photon counting data.

2. The electronics arrangement of claim 1, the counter block configured to:
   responsive to the number of detection events not exceeding the first detection event count threshold for the measurement interval, generate an output based upon the photon counting data but not the integration data.

3. The electronics arrangement of claim 1, the counter block configured to:
   responsive to the number of detection events exceeding the second detection event count threshold for the measurement interval, generate an output based upon the integration data but not the photon counting data.

4. The electronics arrangement of claim 1, the counter block configured to:
   apply a scaling factor to at least one of the integration data or the photon counting data prior to applying the first blending weight and applying the second blending weight to normalize the integration data with respect to the photon counting data.

5. The electronics arrangement of claim 1, the counter block configured to:
   derive the first blending weight and the second blending weight using a linear interpolation blending function, the first blending weight and the second blending weight derived based upon the number of detection events during the measurement interval.

6. The electronics arrangement of claim 5, the linear interpolation blending function comprising a function $w(x)=x$, where x corresponds to a normalized crossover region coordinate.

7. The electronics arrangement of claim 1, the counter block configured to:
   derive the first blending weight and the second blending weight using a first-derivative matching blending function.

8. The electronics arrangement of claim 1, the counter block configured to:
   derive the first blending weight and the second blending weight based upon a first signal to noise and error ratio (SNER) for the integration data and a second SNER for the photon counting data.

9. A method for determining an output for a detector cell of a photon counting detector array, comprising:
   generating integration data indicative of an amount of charge integrated by an integration circuit during a measurement interval based upon a number of resets to the integration circuit during the measurement interval;
   generating photon counting data indicative of a number of detection events identified by a photon counting circuit during the measurement interval;
   responsive to the number of detection events not exceeding a first detection event count threshold for the measurement interval, generating a first output based upon the photon counting data;

responsive to the number of detection events exceeding a second detection event count threshold for the measurement interval, generating a second output based upon the integration data; and responsive to the number of detection events being between the first detection event count threshold and the second detection event count threshold for the measurement interval, generating a blended output based upon the photon counting data and the integration data.

10. The method of claim 9, comprising, responsive to the number of detection events being between the first detection event count threshold and the second detection event count threshold for the measurement interval:

applying a scaling factor to at least one of the integration data or the photon counting data prior to the generating a blended output.

11. The method of claim 9, the generating a blended output comprising:

applying a first blending weight to the integration data to create weighted integration data;

applying a second blending weight to the photon counting data to create weighted photon counting data; and generating the blended output based upon the weighted integration data and the weighted photon counting data, the first blending weight and the second blending weight derived using a linear interpolation blending function.

12. The method of claim 11, wherein the first blending weight and the second blending weight are derived based upon the number of detection events during the measurement interval.

13. The method of claim 9, the generating a blended output comprising:

applying a first blending weight to the integration data to create weighted integration data;

applying a second blending weight to the photon counting data to create weighted photon counting data; and generating the blended output based upon the weighted integration data and the weighted photon counting data, the first blending weight and the second blending weight derived using a first-derivative matching blending function.

14. The method of claim 9, the generating a blended output comprising:

applying a first blending weight to the integration data to create weighted integration data;

applying a second blending weight to the photon counting data to create weighted photon counting data; and generating the blended output based upon the weighted integration data and the weighted photon counting data, the first blending weight and the second blending weight derived based upon a first signal to noise and error ratio (SNER) for the integration data and a second SNER for the photon counting data.

15. A radiation imaging system, comprising:

an ionizing radiation source; and a photon counting detector array comprising one or more detector cells configured to detect radiation from the ionizing radiation source, a first detector cell comprising:

a radiation conversion element configured to convert radiation detected by the first detector cell into charge; and an electronics arrangement comprising:

an integration circuit configured to integrate the charge to generate a voltage signal;

a photon counting circuit configured to identify detection events based upon the voltage signal; and a counter block configured to:

generate integration data indicative of an amount of the charge that is integrated by the integration circuit during a measurement interval based upon a number of resets to the integration circuit during the measurement interval;

generate photon counting data indicative of a number of detection events identified by the photon counting circuit during the measurement interval; and responsive to the number of detection events being between a first detection event count threshold and a second detection event count threshold for the measurement interval, generate a blended output based upon the photon counting data and the integration data.

16. The radiation imaging system of claim 15, the counter block configured to:

apply a scaling factor to at least one of the integration data or the photon counting data prior to generating the blended output to normalize the integration data with respect to the photon counting data.

17. The radiation imaging system of claim 15, the counter block configured to:

responsive to the number of detection events not exceeding the first detection event count threshold for the measurement interval, generate an output based upon the photon counting data but not the integration data; and responsive to the number of detection events exceeding the second detection event count threshold for the measurement interval, generate an output based upon the integration data but not the photon counting data.

18. The radiation imaging system of claim 15, the radiation conversion element comprising a direct conversion material configured to convert the radiation directly into charge.

19. The radiation imaging system of claim 15, the radiation comprising at least one of x-ray radiation or gamma radiation.

20. The radiation imaging system of claim 15, wherein the integration data is weighted relative to the photon counting data prior to generating the blended output to normalize the integration data with respect to the photon counting data.

* * * * *